(12) United States Patent
Rogler et al.

(10) Patent No.: US 8,729,046 B2
(45) Date of Patent: May 20, 2014

(54) MIR27B IS A NOVEL TARGET FOR TREATMENT OF LIVER FIBROSIS

(71) Applicant: Albert Einstein College of Medicine of Yeshiva University, Bronx, NY (US)

(72) Inventors: Leslie E. Rogler, Carmel, NY (US); Charles E. Rogler, Carmel, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/707,055

(22) Filed: Dec. 6, 2012

(65) Prior Publication Data

US 2013/0150428 A1    Jun. 13, 2013

Related U.S. Application Data

(60) Provisional application No. 61/567,918, filed on Dec. 7, 2011.

(51) Int. Cl.
*A61K 48/00* (2006.01)
*C07H 21/04* (2006.01)
*C07H 21/02* (2006.01)

(52) U.S. Cl.
USPC ........ 514/44; 536/23.1; 536/24.3; 536/24.31; 536/24.33; 536/24.5

(58) Field of Classification Search
CPC ....... A61K 31/07; C07H 21/02; C12N 15/113
See application file for complete search history.

(56) References Cited

PUBLICATIONS

Yuan et al. (FEBS Letters, 585, 2011, 927-934).*
Sanderson, N. et al. entitled "Hepatic expression of mature transforming growth factor β1 in transgenic mice results multiple tissue lesions," Proc. Natl. Acad. Sci., vol. 92, pp. 2572-2576, Mar. 1995.
Krutzfeldt J et al., entitled "Silencing of microRNAs in vivo with 'antagomirs,'" Nature, Dec. 1, 2005;438 (7068):685-9, Abstract Only.
Rogler C E et al., entitled "MicroRNA-23b cluster microRNAs regulate transforming growth factor-beta/bone morphogenetic protein signaling and liver stem cell differentiation by targeting Smads," Hepatology, Aug. 2009;50 (2):575-84, Abstract Only.

* cited by examiner

*Primary Examiner* — Amy Bowman
(74) *Attorney, Agent, or Firm* — Amster, Rothstein & Ebenstein LLP

(57) ABSTRACT

Methods are provided for treating fibrosis of a tissue, including fibrosis of the liver, using combinations of antagomirs and/or locked nucleic acids. Compositions therefor are also provided.

10 Claims, 8 Drawing Sheets

SEQUENCE LISTING

<160> NUMBER OF SEQ ID NOS: 9

<210> SEQ ID NO 1
<211> LENGTH: 21
<212> TYPE: RNA
<213> ORGANISM: Artificial Sequence
<220> FEATURE:
<223> OTHER INFORMATION: antagmoir directed to a human miRNA

<400> SEQUENCE: 1
gguaaucccu ggcaauguga u                                              21

<210> SEQ ID NO 2
<211> LENGTH: 21
<212> TYPE: RNA
<213> ORGANISM: Artificial Sequence
<220> FEATURE:
<223> OTHER INFORMATION: antagomir directed to a human mRNA

<400> SEQUENCE: 2
gcagaacuua gccacuguga a                                              21

<210> SEQ ID NO 3
<211> LENGTH: 22
<212> TYPE: RNA
<213> ORGANISM: Artificial Sequence
<220> FEATURE:
<223> OTHER INFORMATION: antagomir directed to a human miRNA

<400> SEQUENCE: 3 cguuccugc ugaacugagc ca                                              22

<210> SEQ ID NO 4
<211> LENGTH: 21
<212> TYPE: RNA
<213> ORGANISM: Homo Sapiens

<400> SEQUENCE: 4
aucacauugc cagggauuac c                                              21

<210> SEQ ID NO 5
<211> LENGTH: 21
<212> TYPE: RNA
<213> ORGANISM: Homo Sapiens

<400> SEQUENCE: 5
uucacagugg cuaaguucug c                                              21

<210> SEQ ID NO 6
<211> LENGTH: 22
<212> TYPE: RNA
<213> ORGANISM: Homo Sapiens

<400> SEQUENCE: 6
uggcucaguu cagcaggaac ag                                             22

<210> SEQ ID NO 7
<211> LENGTH: 21
<212> TYPE: RNA
<213> ORGANISM: Artificial Sequence
<220> FEATURE:
<223> OTHER INFORMATION: Chemically synthesized mismatched anatgomir

<400> SEQUENCE: 7

```
ggucaucucu gguaacguga u                                          21

<210> SEQ ID NO 8
<211> LENGTH: 21
<212> TYPE: RNA
<213> ORGANISM: Artificial Sequence
<220> FEATURE:
<223> OTHER INFORMATION: Chemcially synthesized mismatched antagomir

<400> SEQUENCE: 8
gcagcacuca gcuacuauga a                                          21

<210> SEQ ID NO 9
<211> LENGTH: 21
<212> TYPE: RNA
<213> ORGANISM: Artificial Sequence
<220> FEATURE:
<223> OTHER INFORMATION: Chemically synthesized mismatched antagomir

<400> SEQUENCE: 9
cugcucccgc ugaccucgcc a                                          21
```

MIR27B IS A NOVEL TARGET FOR TREATMENT OF LIVER FIBROSIS

STATEMENT OF GOVERNMENT SUPPORT

This invention was made with government support under grant numbers R01 DK61153 and CA37232 awarded by the National Institutes of Health. The government has certain rights in the invention.

CROSS-REFERENCE TO RELATED APPLICATIONS

This application claims benefit of U.S. Provisional Application No. 61/567,918, filed Dec. 7, 2011, the contents of which are hereby incorporated by reference.

BACKGROUND OF THE INVENTION

Throughout this application various publications, including patents and patent application publications, are referred to by publication number or by a number in square brackets. Full citations for the numbered publications may be found at the end of the specification. The disclosures of each of the publications, patents and patent application publications referred to herein are hereby incorporated by reference in their entirety into the subject application to more fully describe the art to which the subject invention pertains.

Fibrosis of the liver is a widely spread disorder which may be caused by any chronic liver disease. It is a wound healing response comprising reversible scarring that occurs in almost all patients with chronic, but not self-limited liver injury. Ultimately, hepatic fibrosis leads to cirrhosis, characterized by nodule formation and organ contraction. In all circumstances, the composition of the hepatic scar is similar. Moreover, the cells and soluble factors participating in this response in liver are also similar to those participating in parenchymal injury to kidney, lung, or skin.

Fibrosis occurs earliest in regions where injury is most severe. In response to liver injury, hepatic stellate cells undergo an "activation" process in which they lose vitamin A, become highly proliferative, and synthesize "fibrotic" matrix rich in type I collagen, and fibrosis ensues. No effective treatments currently exist.

The present invention address the need for targeted treatments for reversal of fibrosis in a tissue, including fibrosis of the liver.

SUMMARY OF THE INVENTION

A method is provided of treating fibrosis of a tissue in a subject, or of reducing development of fibrosis of a tissue in a subject at risk of fibrosis of a tissue, comprising administering to the subject an amount of a combination of three different molecules, each molecule being, independently, a nucleic acid, or nucleic acid analogue, directed to microRNAs chosen from miR-23b, miR-27b and miR-24, effective to treat fibrosis of the tissue or to reduce development of fibrosis of the tissue.

Also provided is a composition comprising a nucleic acid or nucleic acid analogue directed to microRNAs chosen from miR-23b, miR-27b and miR-24.

In a further aspect of the invention, a nucleic acid or nucleic acid analogue is provided directed to microRNAs chosen from miR-23b, miR-27b and miR-24, effective to treat fibrosis.

In another aspect of the invention a combination of three antagomirs are provided having the following sequences:

```
                                            (SEQ ID NO: 4)
mG*mG*mUmAmAmUmCmCmCmUmGmGmCmAmAmUmGmU*mG*mA*mU*;

(SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*
``` for treating fibrosis of a tissue or for reducing development of fibrosis of a tissue.

In another aspect of the invention, a method is provided of treating fibrosis of a tissue in a subject, or of reducing development of fibrosis of a tissue in a subject at risk of fibrosis of a tissue, comprising administering to the subject an amount of a combination of a retinol and a palmitic acid effective to treat fibrosis of the tissue or to reduce development of fibrosis of the tissue.

DETAILED DESCRIPTION OF THE INVENTION

Figure 1:
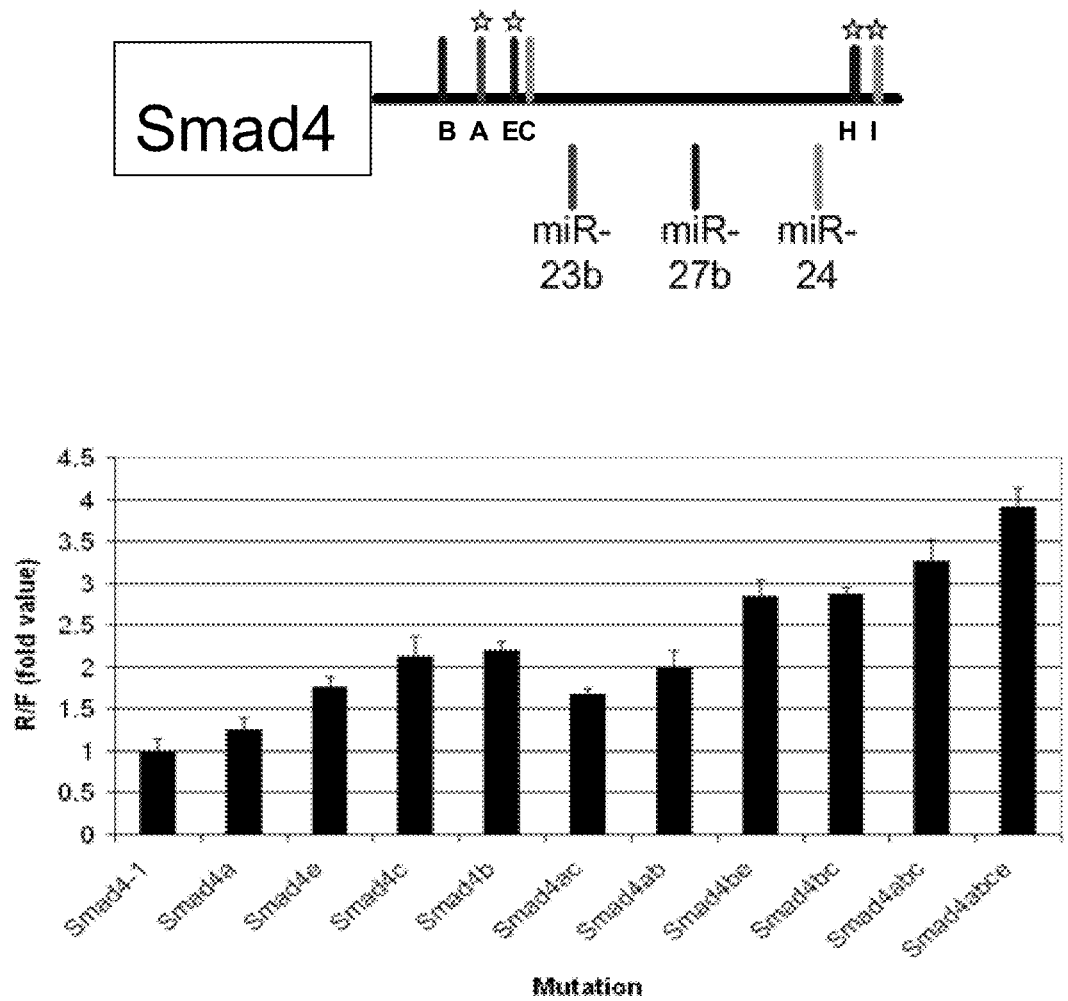
FIG. 1: Mutational analysis of target sites in the Smad 4 3'-UTR confirmed multiple cooperative suppression by miR23b cluster miRs.
Figure 2:
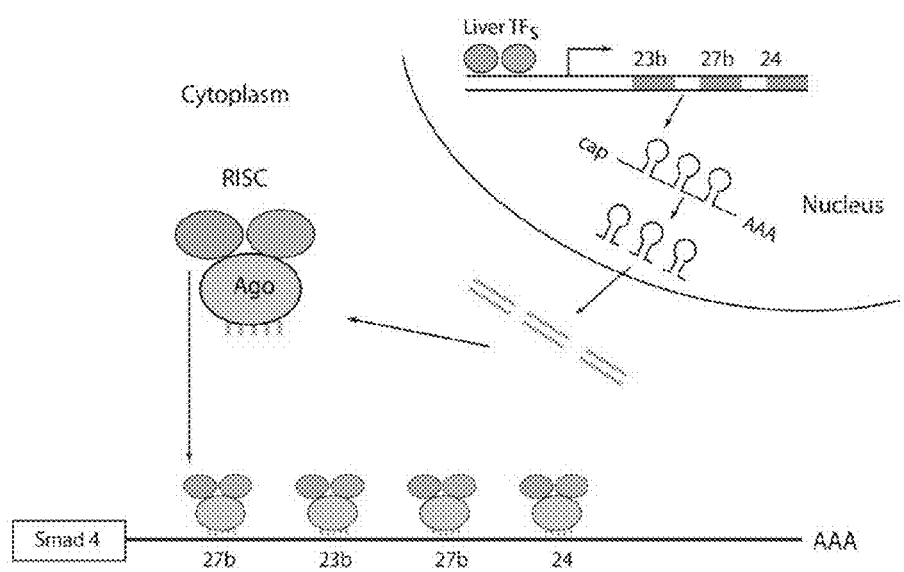
FIG. 2: "Gang of Three" mechanism of cooperative miRNA regulation of Smad 4. In the nucleus, three miRNAs are synthesized from the same locus (23b, 27b and 24). These three miRNAs are processed from the same primary RNA and are transported to the cytoplasm. In the cytoplasm each one becomes attached to Ago. Each of the miRNAs bind to a specific site on the 3' UTR of Smad 4. Translation of the message is blocked 3-4 fold.

A method is provided of treating fibrosis of a tissue in a subject, or of reducing development of fibrosis of a tissue in a subject at risk of fibrosis of a tissue, comprising administering to the subject an amount of a combination of three different molecules, each molecule being, independently, a nucleic acid or nucleic acid analogue directed to microRNAs chosen from miR-23b, miR-27b and miR-24, effective to treat fibrosis of the tissue or to reduce development of fibrosis of the tissue.

In a preferred embodiment, the three different molecules are each directed to a different one of miR-23b, miR-27b and miR-24.

In an embodiment, the three different molecules are nucleic acids, each complementary to the microRNA they are targeted to. In a preferred embodiment, the three different molecules are nucleic acids, each fully complementary to the microRNA they are targeted to. In a most preferred embodiment, the three different molecules are antagomirs, each fully complementary to the microRNA they are targeted to.

Where the three different molecules are nucleic acid analogues, each complementary to the microRNA they are targeted to, the nucleic acid analogues can be analogues relative to a non-analogue nucleic acid by comprising a methylene bridge connecting a 2'-O atom and a 4'-C atom of at least one ribose thereof.

In a preferred embodiment, the nucleic acids are ribonucleic acids. In an embodiment, the nucleic acid analogues are analogues of ribonucleic acid.

In a most preferred embodiment, the miR-23b has the sequence AUCACAUUGCCAGGGAUUACC (SEQ ID NO:1), the miR-27b has the sequence UUCACAGUGGCUAAGUUCUGC (SEQ ID NO:2), and the miR-24 has the sequence UGGCUCAGUUCAGCAGGAACAG (SEQ ID NO:3).

In a most preferred embodiment, three different nucleic acids/nucleic acid analogues have sequences chosen from:

```
                                              (SEQ ID NO: 4)
mG*mG*mUmAmAmUmCmCmCmUmGmGmCmAmAmUmGmU*mG*mA*mU*;

(SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*.
```

In the sequences presented herein, an "m" represents a 2'-O-methyl-sugar modification, and an asterisk represents a phosphorothioate linkage in the backbone.

In a preferred embodiment, one, more than one, or all of the nucleic acids or nucleic acid analogues are, separately, covalently bonded to a cholesterol at their 3' end.

In an embodiment, the tissue is liver, skin, lung or kidney. In a most preferred embodiment, the tissue is liver tissue. In an embodiment, the liver is cirrhosed.

Also provided is a composition comprising a nucleic acid or nucleic acid analogue directed to microRNAs chosen from miR-23b, miR-27b and miR-24. In a preferred embodiment, the composition is a pharmaceutical composition and comprises a pharmaceutically acceptable carrier.

In a most preferred embodiment, the composition comprises three different nucleic acids or nucleic acid analogues comprising one directed to miR-23b, one directed to miR-27b and one directed to miR-24. In a preferred embodiment, the three nucleic acids are each complementary to the microRNA they are targeted to. In a most preferred embodiment, the three different nucleic acids are each fully complementary to the microRNA they are targeted to. In an embodiment, the composition comprises three different are nucleic acid analogues, each complementary to the microRNA they are targeted to, and wherein the nucleic acid analogues are analogues by virtue of comprising a methylene bridge connecting a 2'-O atom and a 4'-C atom of at least one ribose thereof.

In a preferred embodiment, the nucleic acids are ribonucleic acids. In an embodiment, the nucleic acid analogues are analogues of ribonucleic acid.

In a most preferred embodiment, the miR-23b has the sequence AUCACAUUGCCAGGGAUUACC (SEQ ID NO:1), the miR-27b has the sequence UUCACAGUGGCUAAGUUCUGC (SEQ ID NO:2), and the miR-24 has the sequence UGGCUCAGUUCAGCAGGAACAG (SEQ ID NO:3).

In a most preferred embodiment of the composition, the composition following antagomirs:

```
                                              (SEQ ID NO: 4)
mG*mG*mUmAmAmUmCmCmCmUmGmGmCmAmAmUmGmU*mG*mA*mU*;

(SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*.
```

In a further aspect of the invention, a nucleic acid or nucleic acid analogue is provided directed to microRNAs chosen from miR-23b, miR-27b and miR-24 effective to treat fibrosis.

In another aspect of the invention a combination of three antagomirs are provided having the following sequences:

```
                                              (SEQ ID NO: 4)
mG*mG*mUmAmAmUmCmCmCmUmGmGmCmAmAmUmGmU*mG*mA*mU*;

(SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*
``` for treating fibrosis of a tissue or effective to reduce development of fibrosis.

In a preferred embodiment of the nucleic acid or nucleic acid analogue, or in an embodiment of the combination of three antagomirs, the fibrosis is fibrosis of a liver. In an embodiment, the fibrosis of the liver is caused by cirrhosis. In an embodiment, the cirrhosis is caused by alcohol. In an embodiment, the fibrosis of the liver is caused by non-alcoholic fatty liver disease. In an embodiment, the fibrosis of the liver is caused by non-alcoholic steatohepatitis.

Antagonism of the three relevant miRNAs' functions may be achieved by antagomirs (see [2] in relation to the discovery of antagomirs). As used herein, "antagomirs" are single-stranded, oligoribonucleotides, all or some of which can be chemically-modified, that are at least partially complementary to their respective miRNA sequence and which, preferably, are fully complementary thereto. Antagomirs may be synthesized, in a non-limiting example, by using standard solid-phase oligonucleotide synthesis protocols. See U.S. Patent Application Publication Nos. 2007-0123482 A1 and US 2007-0213292 A1 (the disclosures of each of which are incorporated herein by reference).

The antagomirs of the invention may comprise one or more modified nucleotides, such as a nucleotide having a modified sugar thereof. In a non-limiting example, the sugar modification is at the 2'-position. In a non-limiting example, the sugar modification is a 2'-O-methyl-sugar modification. In one embodiment, the sugar modification is chosen from a group consisting of 2'-O-methoxyethyl, 2'-F, 2'-O-[2-(methylamino)-2-oxoethyl], 2'-S-methyl, 2'-O—CH$_2$-(4'-C) and 2'-O—CH$_2$CH$_2$-(4'-C). In some embodiments, antagomirs comprise only modified nucleotides. Antagomirs of the invention may also comprise one or more phosphorothioate linkages resulting in a partial or full phosphorothioate backbone. In one embodiment, the antagomir comprises at least one non-phosphodiester backbone linkage. The non-phosphodiester backbone may occur only at one termini, or only at both termini, or may occur only in terminal regions, e.g., at a position on a terminal nucleotide or in the last 2, 3, 4, 5, or 10 nucleotides of a strand, or may occur at any position or throughout the nucleic acid/analogue. In a preferred embodiment the non-phosphodiester backbone occurs between 1, 2, 3 or 4 contiguous terminal residues at one terminal or at both terminals. In a preferred embodiment the non-phosphodiester backbone is present between the first three terminal residues of the 5' end and also of the last four terminal residues at the 3' end of the antagomir. In one embodiment, the non-phosphodiester backbone linkage is a phosphorothioate, phosphorodithioate, alkyl-phosphonate or phosphoramidate backbone linkage. All of the modifications herein may be also applied to a locked nucleic acid (LNA) of the invention, the antisense oligonucleotides of the invention and to the interference/inhibitory RNA of the invention.

To facilitate in vivo delivery and stability, the antagomir may be linked to a lipophilic steroid, for example a cholesterol moiety, at its 3' end. Antagomirs can also be complexed with an amphipathic moiety. Exemplary amphipathic moieties for use with oligonucleotide agents are described in PCT Application No. PCT/US2004/07070, filed on Mar. 8, 2004. The antagomirs or LNA can be linked to another ligand, for example, a therapeutic modifier, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics, or a protein (e.g., human serum albumin (HSA), low-density lipoprotein (LDL), high-density lipoprotein (HDL), or globulin), a carbohydrate (e.g., a dextran, pullulan, chitin, chitosan, inulin, cyclodextrin or hyaluronic acid), or a lipid. The ligand may also be a recombinant or synthetic molecule, such as a synthetic polymer, e.g., a synthetic polyamino acid, an oligonucleotide (e.g. an aptamer). Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, pseudopeptide-polyamine, peptidomimetic polyamine, dendrimer polyamine, arginine, amidine, protamine, cationic lipid, cationic porphyrin, quaternary salt of a polyamine, or an alpha helical peptide. Ligands can also include targeting groups, e.g., a cell or tissue targeting agent, e.g., a lectin, glycoprotein, lipid or protein, e.g., an antibody for tissue-specific delivery that binds to a specified cell type such as a liver cell (e.g. an activated stellate cell). A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Antagomirs suitable for inhibiting miRNAs may be about 15 to about 50 nucleotides in length, more preferably about 18 to about 30 nucleotides in length, and most preferably about 20 to about 25 nucleotides in length. In an embodiment, each of the plurality antagomirs of the combination treatment are of the same length. In an embodiment, each antagomir of the combination treatment is the same length (in nucleotide residues, i.e. excluding ligands) as the corresponding miRNA they are directed to. In an embodiment, the antagomirs are all 21 nucleotides in length. "Partially complementary" refers to a sequence that is at least about 75%, 80%, 85%, 90%, 95%, 96%, 97%, 98%, or 99% complementary to a target polynucleotide sequence. "Fully complementary" as used herein refers to exact and complete complementarity, i.e. 100%. The antagomirs may be at least about 75%, 80%, 85%, or 90% complementary to a mature miR-23b, miR-27b and miR-24 sequence. In some embodiments, the antagomir may be substantially complementary to a mature miR-23b, miR-27b and miR-24 sequence, that is at least about 95%, 96%, 97%, 98%, or 99% complementary to the target polynucleotide sequence. In other embodiments, the combination of antagomirs are 100% complementary to the mature miRNA sequences of miR-23b, miR-27b and miR-24.

Inhibition of miR-23b, miR-27b and miR-24 function may also be achieved by administering antisense oligonucleotides and/or locked nucleic acid antagonists and both of these are encompassed by the present invention. The antisense oligonucleotides may be ribonucleotides or deoxyribonucleotides. Preferably, the antisense oligonucleotides have at least one chemical modification. Antisense oligonucleotides may comprise of one or more locked nucleic acids, i.e. are modified nucleotides, preferably ribonucleotides, that contain a methylene bridge between the 2' and 4' carbons of the ribose sugar moiety resulting in a "locked" conformation (locked nucleic acids or LNAs) that confers enhanced thermal stability to oligonucleotides containing the LNAs. The resulting LNAs, by being fully complementary or partially complementary to the target miRNAs, are LNA antagonists. Alternatively, the antisense oligonucleotides may comprise one or more peptide nucleic acids (PNAs), which contain a peptide-based backbone rather than a sugar-phosphate backbone.

Other chemical modifications that the antisense oligonucleotides may contain include, but are not limited to, sugar modifications, such as 2'-O-alkyl (e.g., 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Particular antisense oligonucleotides useful for inhibiting the activity of microRNAs are about 19 to about 25 nucleotides in length. Antisense oligonucleotides may comprise a sequence that is at least partially complementary to a mature miR-23b, miR-27b and miR-24 sequence, e.g., at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the combination of antisense oligonucleotides comprise sequences that are 100% complementary to the mature miRNA sequences of miR-23b, miR-27b and miR-24.

MiR-23b, miR-27b and miR-24 may also be inhibited by administering inhibitory RNA molecules each having at least partial sequence identity to one of miR-23b, miR-27b and miR-24. The inhibitory RNA molecules may be double-stranded, small interfering RNA (siRNA) or a short hairpin RNA molecules (shRNA) comprising a stem-loop structure. The double-stranded regions of the inhibitory RNA molecule may comprise a sequence that is at least partially identical, e.g., about 75%, 80%, 85%, 90%, 95%, 96%, 97%, 98%, or 99% identical, to the mature miR-23b, miR-27b and miR-24 sequences. In some embodiments, the double-stranded regions of the inhibitory RNA comprise a sequence that is at least substantially identical to the mature miR-23b, miR-27b and miR-24 sequences. "Substantially identical" refers to a sequence that is at least about 95%, 96%, 97%, 98%, or 99% identical to a target polynucleotide sequence. In other embodiments, the double-stranded regions of the combination of inhibitory RNA molecules may contain 100% identity to the miR-23b, miR-27b and miR-24 sequences.

The nucleobases of the molecules described hereinabove can comprise one or more modifications or substitutions chosen from the following: 2-(halo)adenine, 2-(alkyl)adenine, 2-(propyl)adenine, 2-(amino)adenine, 2-(aminoalkyll)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N_6$-(methyl)adenine, $N^6,N^6$-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil, 4-(thio)pseudouraci-1, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2(thio)-pseudouracil, 1-(aminoalkylaminocarbonylethylenyl)-4-(thio)pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo)thymine, 2-pyridinone, 5-nitroindole, 3-nitropyrrole, 6-(aza)pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, or any O-alkylated or N-alkylated derivatives thereof.

For example, nuclease-resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed.

As used herein, "treating" fibrosis of a tissue means effecting a state where one or more symptoms of the fibrosis or other parameters by which the disease is characterized are reduced, ameliorated, prevented, or reversed at least in part.

In an embodiment, the fibrosis is fibrosis of liver tissue. Liver fibrosis is the excessive accumulation of extracellular matrix proteins including collagen that occurs in most types of chronic liver diseases. Advanced liver fibrosis results in cirrhosis, liver failure, and portal hypertension and often requires liver transplantation. Accordingly, subjects at risk of fibrosis are subjects having a chronic liver disease. In a non-limiting example, such subjects include subjects having chronic viral hepatitis B (CHB), chronic hepatitis C(CHC), non-alcoholic fatty liver disease (NAFLD), and/or alcoholic liver disease (ALD). While the initial cause of the fibrosis is varied, the ultimate mechanism of fibrosis is common and is treatable with the methods disclosed herein. In other embodiments the fibrosis is of a kidney, of a lung or of skin.

The nucleic acids or nucleic acid analogues described herein (including the antagomirs and the LNAs) can be administered to the subject in a pharmaceutical composition comprising a pharmaceutically acceptable carrier. The pharmaceutically acceptable carrier used can depend on the route of administration. As used herein, a "pharmaceutically acceptable carrier" is a pharmaceutically acceptable solvent, a suspending vehicle, for delivering the instant agents to the animal or human subject. The carrier may be liquid or solid and is selected with the planned manner of administration in mind. Liposomes, microspheres and recombinant chylomicrons are also pharmaceutically acceptable carriers. Pharmaceutically acceptable carriers are known in the art, and include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. In a preferred embodiment the pharmaceutical carrier is acceptable for administration into the liver of a mammal and/or into the hepatic blood supply of a mammal.

The nucleic acids or nucleic acid analogues can be administered together or independently in admixtures with suitable pharmaceutical diluents, extenders, excipients, or carriers (collectively referred to herein as a pharmaceutically acceptable carrier) suitably selected with respect to the intended form of administration and as consistent with conventional pharmaceutical practices. In an embodiment, the nucleic acids or nucleic acid analogues are covalently bonded to a molecule to assist their delivery. In an embodiment they are each conjugated to cholesterol. Nanoparticle delivery of the nucleic acids or nucleic acid analogues of the invention may also be employed in the methods recited herein.

Techniques and compositions for making dosage forms useful in the invention are described in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Dosing can be any method or regime known in the art. For example, twice daily, daily, weekly, monthly, as needed, and continuously.

The nucleic acids or nucleic acid analogues of the invention, or pharmaceutical compositions comprising such can be administered enterally, topically or parenterally to the subject. In an embodiment, the nucleic acids or nucleic acid analogues, or pharmaceutical compositions comprising such are administered directly into the tissue of interest, or into blood vessels supplying the tissue of interest. In such an embodiment, the delivery can be effected by cannula, catheter, infusion or direct injection into the tissue of interest, or into blood vessels supplying the tissue of interest. In addition, the nucleic acids or nucleic acid analogues, or pharmaceutical compositions comprising such can be administered into the vicinity of the tissue, e.g. via an intraperitoneal injection. In another embodiment, the nucleic acids, nucleic acid analogues, or pharmaceutical compositions are delivered via vector delivery, such as a viral vector. For example, an antagomir can be expressed in the target tissue by lentivirus-mediated delivery, adenovirus mediated delivery or adeno-associated virus-mediated delivery. A tissue-specific promoter, e.g. a liver-specific promoter (e.g. see the Liver Specific Gene Promoter Database at rulai.cshl.edu/LSPD/), can be used to more specifically target delivery of the antagomir via the viral vector. For example, a tissue-specific and conditionally active RNA polymerase II promoter can be used. In the case of the kidney, a non-limiting delivery method of the antagomirs or LNAs is by renal catheterization. In the case of the skin, a non-limiting delivery method of the antagomirs or LNAs is topically. In the case of the lung, a non-limiting delivery method of the antagomirs or LNAs is via aerosol.

In another aspect of the invention, a method is provided of treating fibrosis of a tissue in a subject, or of reducing development of fibrosis of a tissue in a subject at risk of fibrosis of a tissue, comprising administering to the subject an amount of a combination of a retinol and a palmitic acid effective to treat fibrosis of the tissue or to reduce development of fibrosis of the tissue. In an embodiment, the tissue is liver tissue.

The methods disclosed herein can be used with any mammalian subject. Preferably, the mammal is a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Example

MicroRNAs play pivotal roles in cell differentiation, histogenesis and disease. The miR-23b, 27b and 24-1 cluster located on murine chromosome 13 regulates bipotent differentiation of liver stem/progenitor cells in vitro by downregulating TGF-β signaling in hepatoblasts by specifically targeting Smads 3, 4, and 5. Mutational analysis of target sites in the Smad 4 3'-UTR showed multiple cooperative suppression by miR23b cluster miRs (see FIG. 1).

It was found that miR-23b polycistron miRNAs (miR-23b, miR-27b and miR-24) cooperatively down-regulate TGFβ signaling by targeting key signaling molecules including Smads 3,4,5 and the TGFβ2R. This provides a mechanism for the cell autonomous response to TGFβ signaling observed in the developing liver.

Herein, combinations of antagomirs, or of LNA (locked nucleic acid) antagonists, or both, directed against miR-23b cluster miRNAs, were used to explore their role in late fetal and early postnatal liver histogenesis and in liver fibrosis. Notably, individual antagomirs/LNAs do not reverse or treat fibrosis, a combination directed to all three is required for the observed effects.

Figure 3:
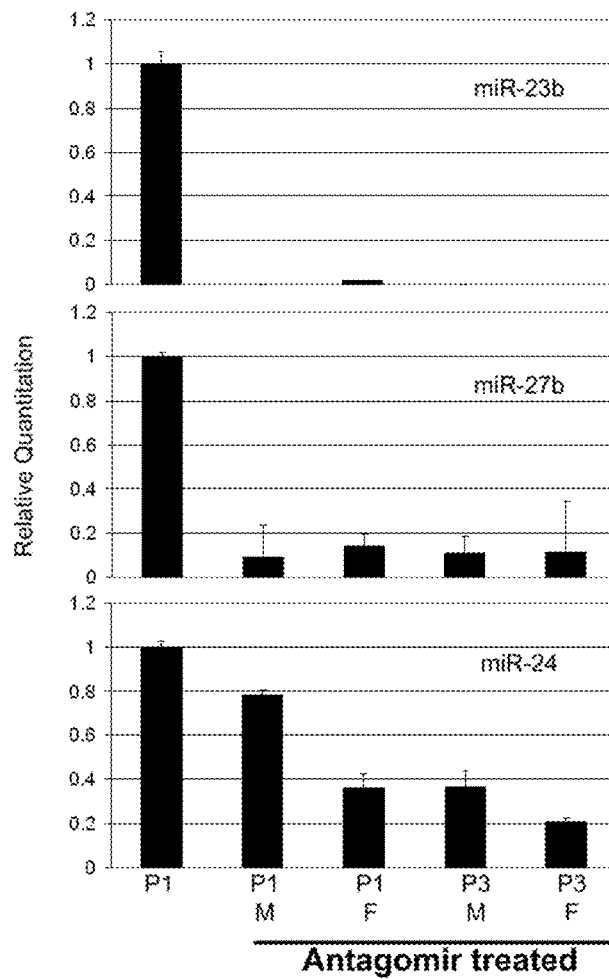
FIG. 3: Treatment with antagomirs directed against miR-23b, miR-27b and miR-24 at P1 effectively reduced steady state levels of these miRNAs.
Figure 4:
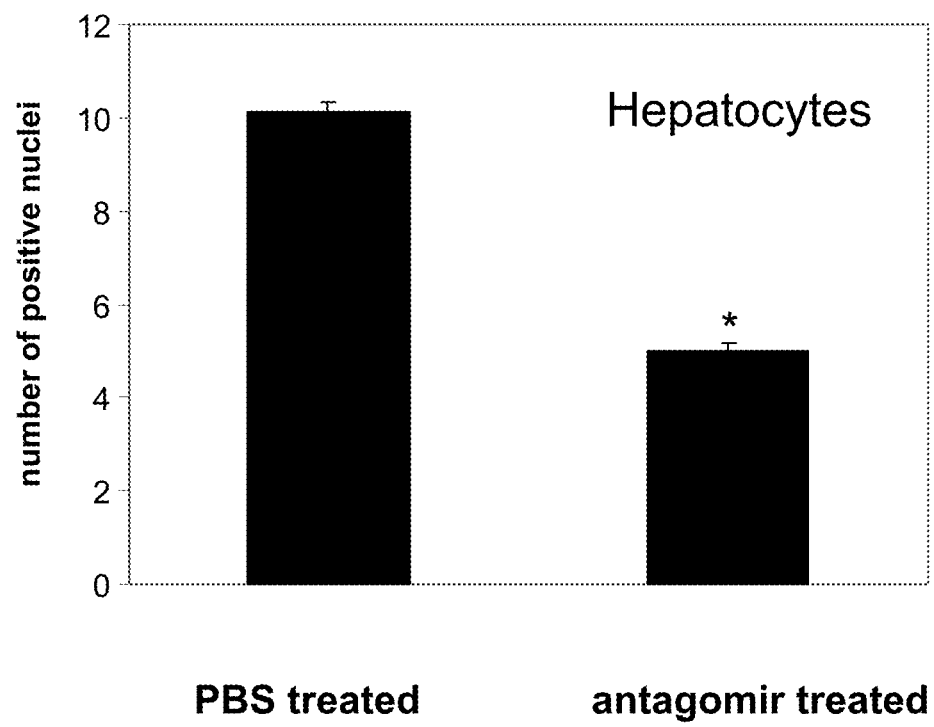
FIG. 4: Post-natal antagomir treatment specifically inhibits the proliferation of Hepatocytes in the neonatal liver.
Figure 5:
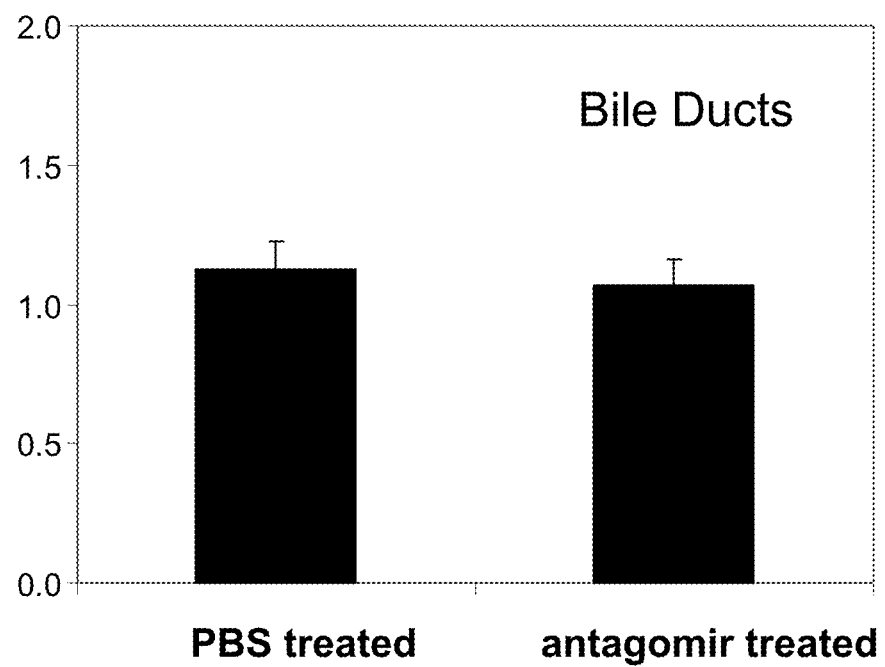
FIG. 5: Post-natal antagomir treatment does not inhibit the proliferation of bile ducts in the neonatal liver.
Figure 6:
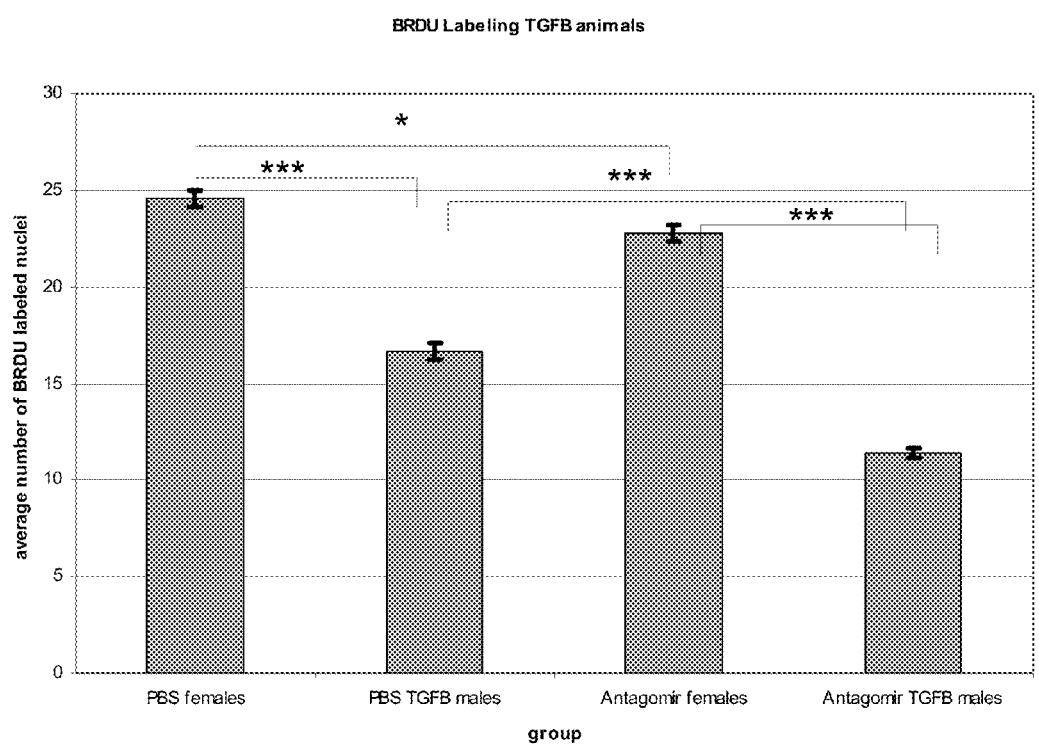
FIG. 6: Antagomir injection promoted the action of TGFβ (i.e. reduction in hepatocyte proliferation).
Figure 7:
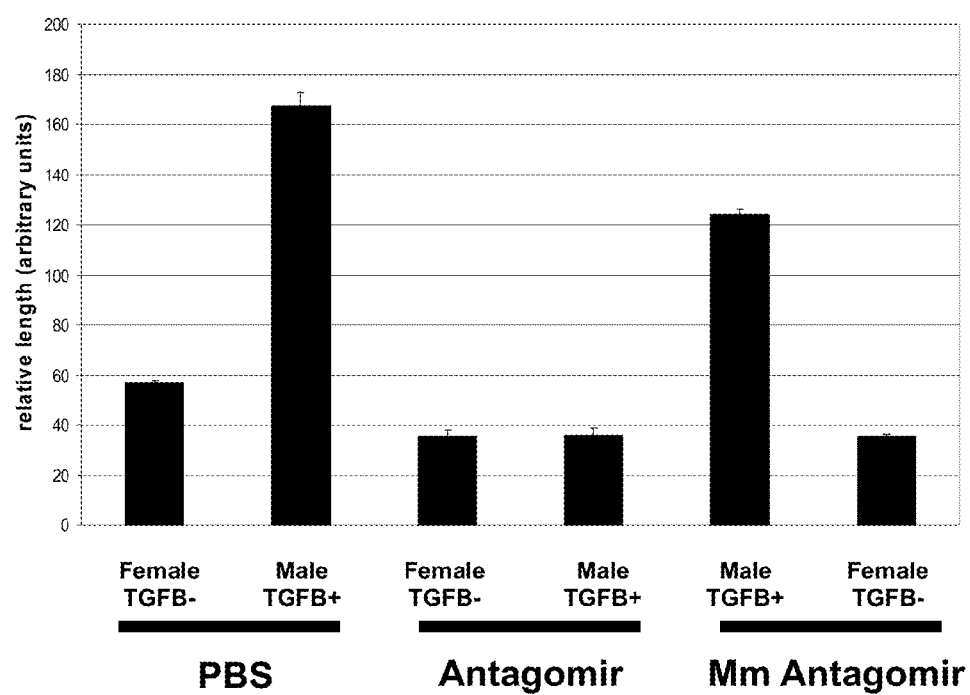
FIG. 7: Antagomir treatment blocks the onset of fibrosis in alb-TGFβ1 transgenic mice.
Figure 8:
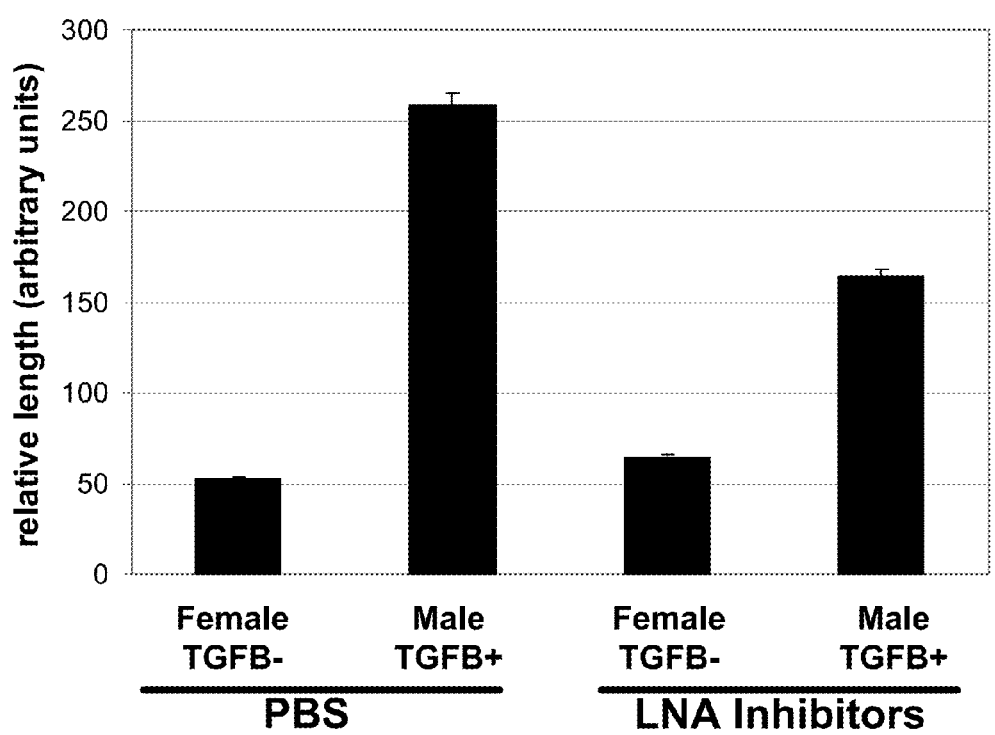
FIG. 8: Treatment with LNA inhibitors can substantially reduce fibrosis.

Intraperitonial injection of antagomirs directed to miR-23b, 27b and 24 (see SEQ ID NOS:4, 6 and 8, respectively) significantly reduced the steady state levels of miR-23b, 27b and 24 one day after injection. Treatment with antagomirs directed against miR-23b, miR-27b and miR-24 at P1 effectively reduces steady state levels of these miRNAs as shown in FIG. 3. The sequences of the antagomirs used are as follows:

(SEQ ID NO: 4)
mG*mG*mUmAmAmUmCmCmCmUmGmGmCmAmAmUmGmU*mG*mA*mU*;

-continued (SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*.

In the sequences presented herein, an "m" represents a 2'-O-methyl-sugar modification, and an asterisk represents a phosphorothioate linkage in the backbone. The LNAs used had the same sequences (i.e. the same as SEQ ID NOS. 4, 6 and 8) but were "locked" by comprising one or more modified ribonucleotides having a methylene bridge between the 2' and 4' carbons of the ribose sugar thereof. In addition, while antagomirs were 3' modified with a cholesterol, the LNAs were not.

The reduction in steady state miRNA persisted for as long as 2 weeks post injection. Injection of Swiss Webster mouse (SW) fetuses at day 16.5 of gestation led to a variable but significant expansion of CK19 positive cells within the fetal liver affirming a role for mir-23b cluster microRNAs in bipotent hepatoblast differentiation in vivo. Injection at postnatal day 1 caused a 50% reduction in BrdU or Ki67 positive hepatocyte nuclei at three weeks of age. The labeling index of cholangiocytes was unaffected by triple antagomir treatment.

In further experiments, alb-TGFβ1 transgenic animals (these mice, developed by Snorri Thorgeirsson's lab, have the transgene located on the Y chromosome so that males are transgenic and females are control. Males develop kidney and liver fibrosis by 2 weeks of age. Kidney fibrosis severe and leads to death in some male transgenics) were injected with either a mix of mir-32b cluster antagomirs or LNA antagonists directed to miR-23b, 27b and 24. A similar repression of hepatocyte proliferation was observed in the TGFβ1 transgenic mice. In addition, at the periphery of the liver there was an expansion of CK19 positive in double thick cords lacking a lumen confirming the results obtained with SW mice.

Male TGFβ1 transgenic mice develop kidney and liver fibrosis which can be detected by reticulin staining [1]. Remarkably, male TGFβ1 mice injected with either the antagomirs combination or LNA antagonist combination showed a striking reduction in liver fibrosis. In addition, injection of triple LNA antagonists into 2-week old animals also caused a significant resolution of fibrosis.

In additional experiments, Mir-23b, 27b and 24 were found to be upregulated in activated hepatic stellate cells compared to freshly isolated cells. Transfection of mir23b cluster antagomirs as described above led to the reactivation of Vitamin A fluorescence. Mock-transfected cells and cells transfected with an irrelevant oligonucleotides (e.g. the following mismatched "antagomirs":

(SEQ ID NO: 5)
mG*mG*mUmCmAmUmCmUmCmUmGmGmUmAmAmCmGmU*mG*mA*mU*;

(SEQ ID NO: 7)
mG*mC*mAmGmCmAmCmUmCmAmGmCmUmAmCmUmAmU*mG*mA*mA*;
and (SEQ ID NO: 9)
mC*mU*mGmCmUmCmCmCmGmCmUmGmAmCmCmUmCmG*mC*mC*mA* for miR-23b, 27b and 24, respectively, did not regain Vitamin A fluorescence.

Further experiments were performed. Hepatic stellate cells (HSCs) transform into activated fibroblasts during the onset of fibrosis, producing fibrous matrices and irreversible, rigid scar tissue; currently, the only feasible treatment is liver transplantation. As stellate cells become activated through this epithelial to mesenchymal transition, they lose the ability to store Vitamin-A in the form of retinol esters, mainly retinylpalmitate. A study was performed to determine whether cells could be reverted back to the normal quiescent state with retinol and palmitic acid treatments or with the transfection of miRNA inhibitors, in the form of stable, antisense expressing miRZip plasmids. The combination treatment of LX2 cells with retinol and palmitic acid restored the ability of the cells to uptake lipid droplets. The combination treatment alone resulted in the reduction of ACTA2 and COL1A, which both marked the reversion of activated stellate cells to the quiescent state. Additionally, there was a clear reduction in the levels of miR-23b, miR-24, and miR-27b. The next part of the study examined whether down regulation of the miR-23b cluster could result in the same alterations in cell phenotype and gene expression. The down regulation of the miR-23b cluster alone was able to dramatically change gene expression levels in a way indicative of a reversion to the quiescent phenotype. Thus, the study confirmed that palmitic acid and retinol treatments could revert stellate cells to a more normal state, and found that miR-23b and miR-27b have the ability to revert cells to the quiescent state. This further supports the use of a pharmaceutical mechanism to revert activated stellate myofibroblasts to the quiescent state in cirrhosis, reducing cell proliferation and scarring.

Discussion

These results indicate that the multiple miR23b cluster microRNAs play a necessary and sufficient role in genesis of fibrosis and are an important target for anti-fibrotic therapy. MiR-23b cluster microRNAs have cell type-specific effects. As shown herein, their down-regulation in developing cholangiocytes permits bile duct formation, and upregulation in hepatocytes allows hepatocyte growth in the neonatal liver and up-regulation in adult hepatic stellate cells leads to activation and fibrosis. Their inhibition by combination of antagomirs and/or LNA antagonists directed to miR-23b, miR-27b and miR-24 treats liver fibrosis in vivo. Unexpectedly, a nearly complete blockage of the TGFβ3-induced fibrosis that normally occurs in the alb-TGFβ1 transgenic mouse livers was also observed. This indicates that the antagomirs had a different effect on hepatic stellate cells whose activation is needed for fibrosis, than on hepatocytes and bile ducts.

REFERENCES

1. Sanderson, N., Factor, V., Nagy, P., Kopp, J., Kondaiah, P., et al., *Hepatic expression of mature transforming growth factor beta 1 in transgenic mice results in multiple tissue lesions*. Proceedings of the National Academy of Sciences of the United States of America, 1995. 92(7): p. 2572-2576

2. Krutzfeldt et al. *Silencing of microRNAs in vivo with 'antagomirs'*, Nature, 438:685-689, 2005.

What is claimed is:

1. A method of treating liver fibrosis in a subject, or of reducing development of liver fibrosis of a tissue in a subject at risk of liver fibrosis, comprising administering to the subject an amount of a combination of three different molecules, each molecule being, independently, a nucleic acid or nucleic acid analogue targeted to microRNAs chosen from miR-23b, miR-27b and miR-24, wherein the combination comprises three different molecules each directed to a different one of miR-23b, miR-27b and miR-24, effective to treat liver fibrosis or to reduce development of liver fibrosis.

2. The method of claim 1, wherein the three different molecules are nucleic acids, each complementary to the microRNA it is targeted to.

3. The method of claim 2, wherein the nucleic acids are antagomirs, each fully complementary to the microRNA it is targeted to.

4. The method of claim 1, wherein the three different molecules are nucleic acid analogues, each complementary to the microRNA they are targeted to, wherein the nucleic acid analogues are analogues by virtue of comprising a methylene bridge connecting a 2'-O atom and a 4'-C atom of at least one ribose thereof.

5. The method of claim 4, wherein the three different nucleic acids analogues are each fully complementary to the microRNA they are targeted to.

6. The method of claim 1, wherein the nucleic acids are ribonucleic acids.

7. The method of claim 1, wherein the miR-23b has the sequence AUCACAUUGCCAGGGAUUACC (SEQ ID NO:1), wherein the miR-27b has the sequence UUCACAGUGGCUAAGUUCUGC (SEQ ID NO:2), and wherein the miR-24 has the sequence UGGCUCAGUUCAGCAGGAACAG (SEQ ID NO:3).

8. The method of claim 1, wherein the three different molecules have sequences chosen from:

(SEQ ID NO: 4)
mG*mG*mUmAmAmUmCmCmCmUmGmGmCmAmAmUmGmU*mG*mA*mU*;

(SEQ ID NO: 6)
mG*mC*mAmGmAmAmCmUmUmAmGmCmCmAmCmUmGmU*mG*mA*mA*;
and (SEQ ID NO: 8)
mC*mU*mGmUmUmCmCmUmGmCmUmGmAmAmCmUmGmAmG*mC*mC*mA*.

9. The method of claim 1, wherein one, more than one, or all of the nucleic acids or nucleic acid analogues are covalently bonded to a cholesterol at their 3' end.

10. The method of claim 1, wherein the liver is cirrhosed.

* * * * *